United States Patent
Diep

(10) Patent No.: US 10,659,000 B2
(45) Date of Patent: May 19, 2020

(54) FLUIDIC SENSOR DEVICE HAVING UV-BLOCKING COVER

(71) Applicant: QORVO US, INC., Greensboro, NC (US)

(72) Inventor: Buu Quoc Diep, Murphy, TX (US)

(73) Assignee: Qorvo Biotechnologies, LLC, Plymouth, MN (US)

(*) Notice: Subject to any disclaimer, the term of this patent is extended or adjusted under 35 U.S.C. 154(b) by 455 days.

(21) Appl. No.: 15/470,111

(22) Filed: Mar. 27, 2017

(65) Prior Publication Data
US 2017/0294892 A1     Oct. 12, 2017

Related U.S. Application Data

(60) Provisional application No. 62/313,301, filed on Mar. 25, 2016.

(51) Int. Cl.
| | |
|---|---|
| H03H 9/10 | (2006.01) |
| B01L 3/00 | (2006.01) |
| H03H 9/02 | (2006.01) |
| H03H 9/17 | (2006.01) |
| H03H 9/13 | (2006.01) |
| H03H 3/02 | (2006.01) |

(Continued)

(52) U.S. Cl.
CPC ....... *H03H 9/02015* (2013.01); *B01L 3/5027* (2013.01); *B01L 3/502707* (2013.01); *G01N 29/022* (2013.01); *G01N 29/036* (2013.01); *G01N 29/222* (2013.01); *G01N 33/54373* (2013.01); *H03H 3/02* (2013.01); *H03H 9/105* (2013.01); *H03H 9/1007* (2013.01); *H03H 9/131* (2013.01); *H03H 9/175* (2013.01); *G01N 29/24* (2013.01); *G01N 2291/0255* (2013.01); *G01N 2291/0256* (2013.01); *G10K 11/04* (2013.01); *H03H 2003/027* (2013.01); *H03H 2009/155* (2013.01)

(58) Field of Classification Search
None
See application file for complete search history.

(56) References Cited

U.S. PATENT DOCUMENTS

| | | |
|---|---|---|
| 4,640,756 A | 2/1987 | Wang et al. |
| 2017/0052174 A1* | 2/2017 | Branch .............. G01N 33/5438 |
| 2017/0110300 A1 | 4/2017 | McCarron et al. |

OTHER PUBLICATIONS

U.S. Appl. No. 15/334,459, filed Oct. 26, 2016, Ryder et al.

* cited by examiner

*Primary Examiner* — Neil N Turk
(74) *Attorney, Agent, or Firm* — Mueting, Raasch & Gebhardt, P.A.

(57) ABSTRACT

A fluidic sensing device includes a first sidewall, a second sidewall, a bulk acoustic resonator structure, a biomolecule, and a cover. A fluidic channel is defined between the first and second sidewalls. The bulk acoustic resonator structure has a surface defining at least a portion of the bottom of the channel. The biomolecule is attached to the surface of the bulk acoustic resonator that forms the bottom of the channel. The cover is disposed over the channel and the first and second sidewalls. A portion of the cover disposed over the channel defines at least a portion of the top of the channel and blocks UV radiation from being transmitted through the cover. A first portion of the cover disposed over the first sidewall is transparent to UV radiation, and a second portion of the cover disposed over the second sidewall is transparent to UV radiation.

12 Claims, 13 Drawing Sheets

(51) Int. Cl.
*G01N 33/543* (2006.01)
*G01N 29/02* (2006.01)
*G01N 29/22* (2006.01)
*G01N 29/036* (2006.01)
G01N 29/24 (2006.01)
H03H 9/15 (2006.01)
G10K 11/04 (2006.01)

FLUIDIC SENSOR DEVICE HAVING UV-BLOCKING COVER

RELATED APPLICATION

This application claims the benefit of U.S. Provisional Patent Application No. 62/313,301, which was filed on Mar. 25, 2016, which provisional patent application is hereby incorporated herein by reference in its entirety to the extent that it does not conflict with the disclosure presented herein.

TECHNICAL FIELD

The present disclosure relates to fluid acoustic wave sensor devices, including fluidic acoustic wave sensor devices having biomolecules configured to bind an analyte.

BACKGROUND

Fluidic devices having acoustic wave sensors for detecting the presence of an analyte in a sample often have biomolecules, such as antibodies or other proteins such as receptors, polynucleic acids, or the like attached to their surfaces. The analyte may bind to the biomolecule attached to the surface of the sensor and increase the mass bound to the sensor. The increased mass alters the wave propagation characteristics (e.g., magnitude, frequency, phase, etc.) of the sensor. The change in propagation characteristics due to analyte binding may be correlated with the amount of bound analyte and, thus, the amount of analyte in the sample.

Many fluidic acoustic wave sensor devices have a cover over a channel through which fluid containing an analyte may flow. A surface of the sensor to which the biomolecule is attached may be exposed to the channel to allow analyte to bind the biomolecule as the fluid flows over the sensor.

The cover is typically placed over the channel after the sensor is functionalized (the biomolecule is attached to the sensor). Once the surface of the sensor is functionalized with the biomolecule, further processing of the sensor or fluidic device should be performed at low temperatures, such as temperatures below 40° C., to limit damage to the biomolecules. Accordingly, higher temperature processing steps to attach the lid over the channel are preferably avoided.

One commonly used low-temperature bonding approach is the use of ultraviolet (UV)—curable epoxy. However, exposure of biomolecules to UV radiation may also degrade or adversely alter the biomolecule.

SUMMARY

The present disclosure relates to, among other things, fluidic acoustic sensor devices and to methods for fixing a cover over a channel of a fluidic acoustic sensor device without destroying biomolecules attached to a surface of the sensor. The methods and devices described herein employ covers having a portion that blocks UV radiation used cure an adhesive and a portion that transmits UV radiation used to cure the adhesive. The portion that blocks the UV radiation is disposed over the channel and prevents exposure of a biomolecule attached to a sensor surface from being exposed to a substantial amount of UV radiation. The portion that transmits the UV radiation is configured to be aligned with a top of a sidewall on which a UV-curable adhesive is disposed.

In some aspects described herein, a fluidic sensing device includes a first sidewall, a second sidewall, a bulk acoustic resonator structure, a biomolecule, and a cover. A fluidic channel is defined between the first and second sidewalls. The bulk acoustic resonator structure has a surface defining at least a portion of the bottom of the channel. The biomolecule is attached to the surface of the bulk acoustic resonator that forms the bottom of the channel. The cover is disposed over the channel and the first and second sidewalls. A portion of the cover disposed over the channel defines at least a portion of the top of the channel and blocks UV radiation from being transmitted through the cover. A first portion of the cover disposed over the first sidewall is transparent to UV radiation, and a second portion of the cover disposed over the second sidewall is transparent to UV radiation. The cover may be attached to a top of surface of the first sidewall and to a top surface of the second sidewall via a cured UV-curable adhesive.

In some aspects described herein, a method for forming a fluidic sensing device includes providing an assembly comprising a first sidewall and a second sidewall, a bulk acoustic resonator structure, and a biomolecule. A fluidic channel is defined between the first sidewall and the second sidewall. The bulk acoustic resonator structure has a surface defining at least a portion of the bottom of the channel. The biomolecule is attached to the surface of the bulk acoustic resonator that defines the bottom of the channel.

The method further comprises providing a cover comprising a first portion configured to be disposed over a top surface of the first sidewall, a second portion configured to be disposed over a top surface of the second sidewall, and a blocking portion configured to be disposed over the channel. The blocking portion is configured to block transmission of UV-radiation configured to cure the adhesive. The first and second portions of the cover are configured to transmit radiation configured to cure the adhesive.

The method also includes disposing a UV curable adhesive on the top surface of the first sidewall and on a top surface of the second sidewall or disposing the UV curable adhesive on an inner surface of the cover along the first and second portions.

The method further comprises placing the cover on the top surfaces of the first and second sidewalls such that the adhesive is between the cover and the first and second sidewalls and such that the first portion of the cover is disposed over the first sidewall, the second portion of the cover is disposed over the second sidewall, and the blocking portion of the cover is disposed over the channel. The method also includes exposing an outer surface of the cover to radiation configured to cure the adhesive such that the radiation is transmitted through the first and second portions of the cover and is blocked from transmission through the blocking portion of the cover.

The methods described herein allow for fixing a cover to a fluidic bulk acoustic wave sensor device without destroying biomolecules attached to a surface of the sensor as the cover is fixed to the surfaces. The resulting fluidic bulk acoustic wave sensing devices contain biomolecules that retain their ability to bind analyte in a fluid flowed over the sensor.

In some aspects described herein, a wafer-scale device for forming a plurality of fluid sensing devices includes a surface forming at least a portion of a plurality of bulk acoustic resonator structures; a biomolecule attached to the portions of the surface forming the bulk acoustic resonator structures; and a plurality of walls extending from the surface, wherein the walls define lateral boundaries of each of the bulk acoustic resonator structures. The device further comprises a ultraviolet (UV)-curable adhesive on the walls; and a cover disposed over the walls and attached to the walls by the adhesive. Portions of the cover disposed over the surface of the wafer to which the biomolecule is attached blocks transmission of ultraviolet (UV) radiation. Portions of the cover disposed over the walls are transparent to UV radiation configured to cure the adhesive.

Those skilled in the art will appreciate the scope of the present disclosure and realize additional aspects thereof after reading the following detailed description in association with the accompanying drawings.

BRIEF DESCRIPTION OF THE DRAWINGS

The accompanying drawing figures incorporated in and forming a part of this specification illustrate several aspects of the disclosure and, together with the description, serve to explain one or more principles of the disclosure.

Figure 1:
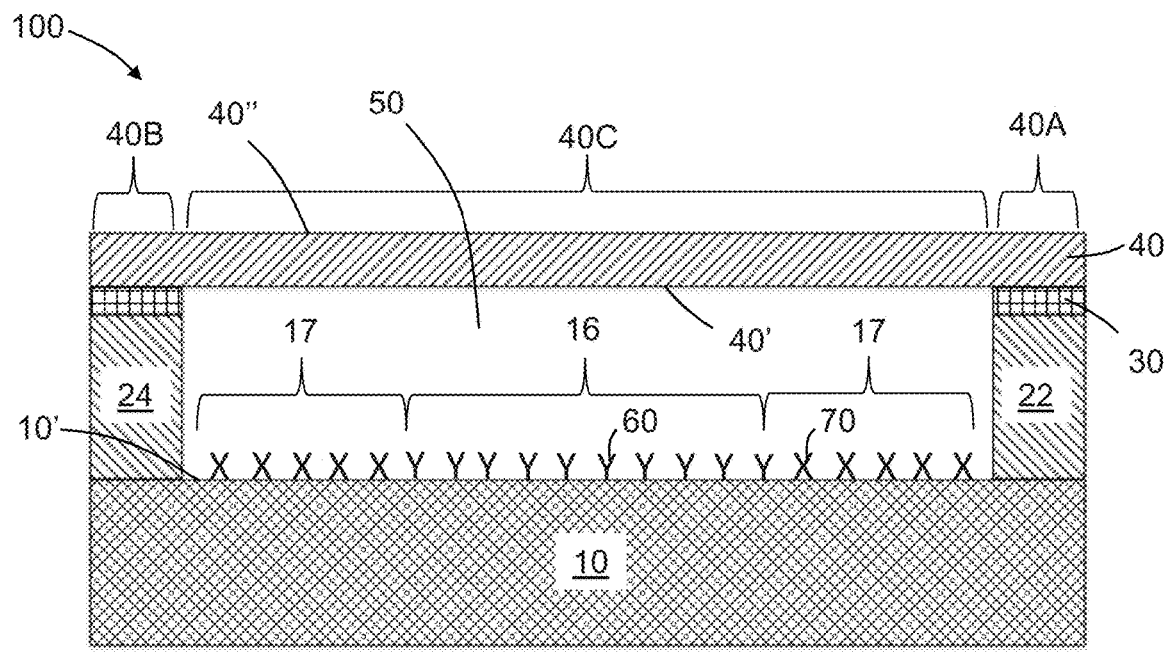
FIG. 1 is a schematic cross sectional view of an embodiment of a microfluidic sensor.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

The present disclosure relates to fluid acoustic wave sensor devices, including fluidic acoustic wave sensor devices having biomolecules configured to bind an analyte. More particularly, the present disclosure relates to (i) processes for assembling fluidic devices including an acoustic resonator structure having a biomolecule attached to a surface of the structure where the assembly process does not destroy or substantially impair function of the biomolecule, and (ii) fluidic devices resulting from the processes. Even more particularly, the present disclosure relates to microfluidic acoustic sensor devices and to methods for fixing a cover over a channel of a microfluidic acoustic sensor device without destroying biomolecules attached to a surface of the sensor.

The methods and devices described herein employ covers having a portion that blocks UV radiation used to cure an adhesive and a portion that transmits UV radiation used to cure the adhesive. The portion that transmits UV radiation may do so over a broad or narrow band of UV radiation, preferably over a broad band. The portion that blocks (e.g., reflects or absorbs) the UV radiation is disposed over the channel and prevents exposure of a biomolecule attached to a sensor surface from being exposed to a substantial amount of UV radiation. The portion that transmits the UV radiation is configured to be aligned with a top of a sidewall on which a UV-curable adhesive is disposed.

The methods described herein may apply to any suitable sensor device employing a biomolecule. For purposes of the present disclosure, a "biomolecule" or "biological molecule" refers to a molecule comprising a polypeptide, such as a protein, or a polynucleic acid, such as DNA or RNA. Preferably the biomolecule comprises a polypeptide. In various embodiments, the biomolecule comprises an antibody or an antigen-binding fragment thereof. For purposes of the remainder of this disclosure and the claims that follow, an "antibody" refers collectively to antibodies and antigen-binding fragments thereof.

In some embodiments, the fluidic devices described herein are analytical devices that include a biomolecule and a transducer that converts an event of binding of a target to the biological molecule into an electrical signal. Certain devices involve a selective interaction between a biomolecule and a target. For example, the biomolecule may be a specific binding material (e.g., an antibody, a receptor, a ligand, etc.) and the target may a molecule, a protein, a DNA, a virus, a bacteria, etc. A binding event or a plurality of binding events between the specific binding material and the target may be converted into a measurable quantity by a transducer. In other embodiments, sensors may utilize a non-specific binding material capable of binding multiple types or classes of molecules or other moieties that may be present in a sample, such as may be useful in chemical sensing applications.

Any suitable fluidic sensing device may be employed in accordance with the teachings presented herein. Preferably, the sensing devices are acoustic wave devices. An acoustic wave device employs an acoustic wave that propagates through or on the surface of a piezoelectric material, whereby changes to the characteristics of the propagation path affect the velocity and/or amplitude of the wave. Presence of a biomolecule on or over an active region of an acoustic wave device permits an analyte to be bound to the biomolecule, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the acoustic wave device and can be correlated to a physical quantity being measured.

The acoustic wave devices describe herein may include a piezoelectric crystal resonator. With such devices, an acoustic wave may embody either a bulk acoustic wave (BAW) propagating through the interior of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength.

BAW devices typically involve transduction of an acoustic wave using electrodes arranged on opposing top and bottom surfaces of a piezoelectric material. In a BAW device, three wave modes may propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids. BAW devices include bulk acoustic resonators deposited on one or more reflective layers, such as Bragg mirror, and film bulk acoustic resonators having an air-gap.

The fluidic sensing device described herein may employ any suitable piezoelectric thin film. Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material layer arranged between electrodes, a polarization axis in a piezoelectric thin film is generally non-perpendicular to (e.g., tilted relative to) the film plane. In sensing applications involving liquid media, the shear component of the resonator is preferably used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof. Conversely, a piezoelectric material grown with a c-axis orientation that is perpendicular relative to a face of an underlying substrate will exhibit a dominant longitudinal response upon application of an alternating current signal across electrodes thereof.

Referring now to FIG. 1, a schematic sectional view of a portion of a fluid sensing device 100 is shown. The device 100 includes a first sidewall 22 and a second sidewall 24. While shown as separate structures, it will be understood that the first 22 and second 24 sidewalls may be formed from one continuous sidewall. Whether one structure or separate structures, the first 22 and second 24 sidewalls define a fluidic channel 50. The device 100 also includes a bulk acoustic resonator structure 10 having a surface 10' defining at least a portion of the channel 50. A biomolecule 60 is attached to the surface 10' of the resonator structure 10, such that the biomolecule 60 is in fluid communication with the fluidic channel 50. Accordingly, when a sample containing a target analyte is flowed through the channel, the target analyte may bind to the biomolecule 60 and add mass to the surface of the resonator structure 10. The change of mass may be transduced by the resonator structure 10 to produce an electrical signal that correlates to the change in mass.

The biomolecule 60 may be applied to all or a portion of the surface 10' of the resonator structure 10. If applied to less than all of the surface 10' a blocking material 70 may be applied to those portions of the surface 10' to which the biomolecule 60 is not bound. Further information on processes that may be employed to coat portion of a surface 10' of a resonator structure 10 and to block a portion of a surface 10' of a resonator structure 10 is provided in U.S. patent application Ser. No. 15/334,459, filed on Oct. 26, 2016, which application is hereby incorporated herein by reference in its entirety to the extent that it does not conflict with the disclosure presented herein.

In the depicted embodiment, the biomolecule 60 is attached to the surface 10' in an active zone 16 of the resonator structure 10, and the blocking material 70 is disposed on less active portions 17 of the surface 10' of the resonator structure 10. Additional information regarding active zones of resonator structures is described in U.S. patent application Ser. No. 15/334,459, filed on Oct. 26, 2016.

The device 100 includes a cover 40 having a portion 40A disposed over the first sidewall 22, a portion 40B disposed over the second sidewall 24, and a portion 40C disposed over the fluidic channel 50. The cover has in inner surface 40' that defines at least a portion of the channel 50 and has an outer surface 40". The cover 40 includes a first portion 40A disposed over the first sidewall 22, has a second portion 40B disposed over the second sidewall 24, and has a portion 40C disposed over the channel 50. The first 40A and second 40B portions of the cover 40 are transparent to UV-radiation. The portion 40C of the cover 40 disposed over the channel 50 blocks transmission of UV-radiation.

As used herein, a "UV-transparent" portion of a cover means that the cover has a percent transmittance (% T) of 60% T or more of radiant energy having a wavelength in a range from 200 nm to 400 nm. For example, the cover may have % T for UV radiation of 80% T or more. Preferably, the cover has a % T of 90% T or more, or 95% T or more.

As used herein, a "UV-blocking" portion of a cover means that the cover has a % T of 30% T or less of radiant energy having a wavelength in a range from 200 nm to 400 nm. For example, the cover may have a % T for UV radiation of 20% T or less. Preferably, the cover has a % T of 10% T or less, or 5% T or less, 3% T or less, 2% T or less or 1% T or less.

Referring again to FIG. 1, the cover 40 may be fixed by adhesive 30 disposed on top of the first sidewall 22 and the second sidewall 24. The adhesive 30 may comprise UV-curable adhesive. Exposure of the external surface 40" of the cover 40 will result in UV radiation being transmitted through the first 40A and second 40B portions of the cover to the adhesive to cure the adhesive and bond the cover 40 to the first 22 and second 24 sidewalls, while transmission of the UV radiation through the portion 40C of the cover over the channel 50 will be blocked to protect the biomolecule 60 attached to the surface 10' of the resonator structure 10 from the potentially damaging effects of the UV radiation.

Figure 2:
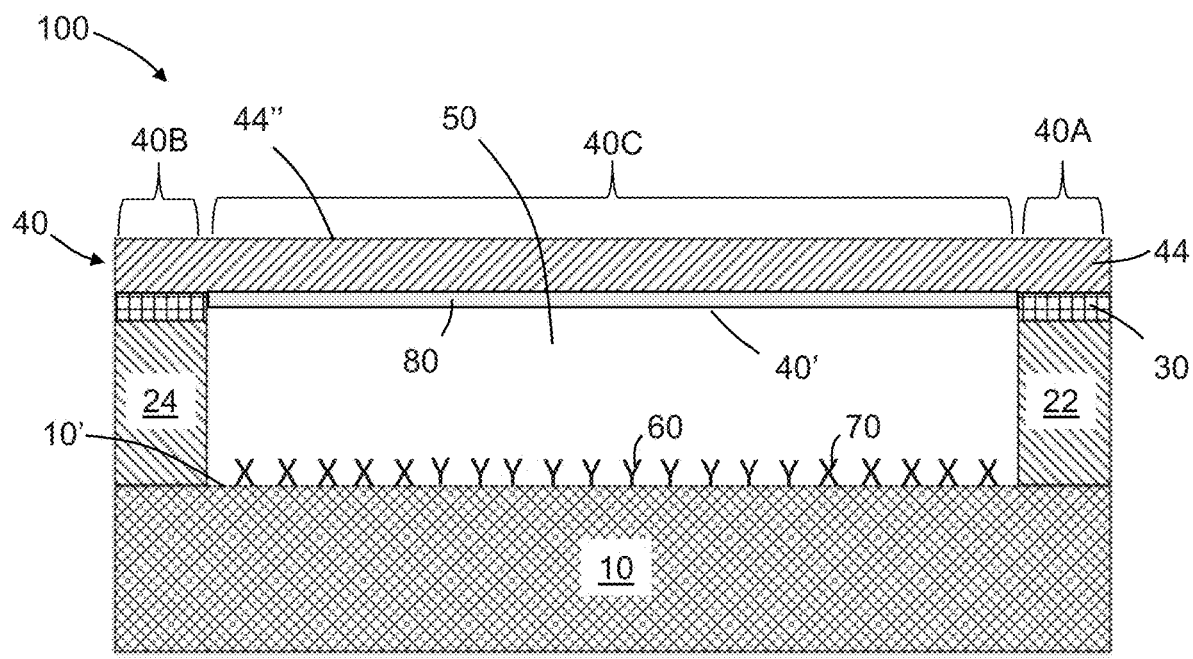
FIG. 2 is a schematic cross sectional view of an embodiment of a microfluidic sensor.

Referring now to FIG. 2, the fluidic device 100 includes a cover 40 comprising a UV blocking coating 80. In the embodiment depicted in FIG. 2, the coating 80 is disposed on an inner surface of a substrate 44 and forms the inner surface 40' of the cover 40'. In some embodiments (not depicted), a UV-blocking coating is disposed on the outer surface 44" of the substrate 44 (at portion 40C) and not on the inner surface of the substrate 44. In some embodiments (not depicted), a UV-blocking coating is disposed on both the outer surface 44" of the substrate 44 (at portion 40C) and on the inner surface of the substrate 44 (at portion 40C).

Preferably, the UV-blocking coating 80 is disposed on the inner surface 44' of the substrate 44 (or the inner surface and the outer surface). Having the UV-blocking coating on the inner surface 44 of the substrate 44 allows less angled UV rays to pass through the cover 40 to react with the biomolecule 60. The closer the coating 80 is to the surface 10' to be protected, the more collimated effect it provides.

Preferably, the substrate 44 is transparent to UV-radiation. Any suitable UV-transparent substrate may be employed to form the cover 40. For example, the substrate 44 may comprise UV-transparent glass or UV-transparent polymeric material. Examples of UV-transparent polymer materials include cyclic olefin copolymers (COC) such as COC sold under the tradename TOPAS®, acrylic polymers, polymethylpentene (PMP), and the like.

Any suitable UV-blocking coating may be applied to the substrate 44 in the region 40C of the cover 40 over the channel 50. The UV-blocking coating 80 may be transparent to visible light or may block transmission of visible light. The coating 80 may comprise one or more compound that absorbs or reflects UV radiation. Examples of compounds that absorb UV radiation include benzophenone, benzophenone derivatives, or other phenol containing compound that absorbs UV light and certain metal oxides such as zinc oxide, titanium oxide, silicon oxide and cerium oxide. In some embodiments, nano-sized particles of one or more metal oxide are used. The one or more UV-absorbing compounds may be incorporated into a polymeric material and coated on the surface of the substrate 44 to block transmission of UV radiation through the portion 40C of the cover 40 configured to be disposed over the microfluidic channel 50.

Examples of coatings 80 that reflect UV radiation include metallic coatings, such as chrome coatings, aluminum coatings, and duralumin coatings. Metal oxides, such as those described above, may also serve to reflect UV radiation. In addition, stacking, thickness and index matching of layers of a multilayer cover may be varied to permit or block transmission of UV radiation.

The UV-blocking coating 80 may be applied to the substrate 44 in any suitable manner. For example, the UV blocking material may be applied by a process including, but not limited to, spray coating, float coating, plasma deposition, vapor deposition, and sputtering.

The first 40A and second 40B portions of the cover 40 may be masked as the portion 40C of the cover 40 configured to be disposed over the channel 50 is coated. The mask may be removed, leaving the first 40A and second 40B uncoated portions transparent to UV radiation due to the transparent nature of the substrate 44, while the coated portion 40C of the cover 40 exhibits UV blocking properties due to the UV-blocking coating 80.

For numbered components depicted in FIG. 2 that are not explicitly discussed with regard to FIG. 2, reference is made to the description above regarding FIG. 1.

Figure 3:
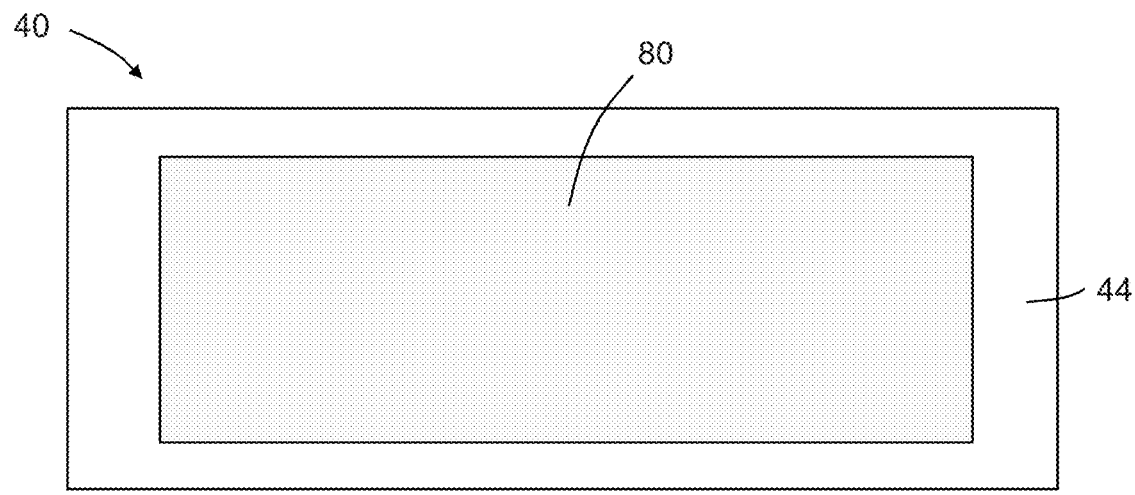
FIG. 3 is a schematic top plan view of an embodiment of an embodiment of a cover for a microfluidic sensor.

Referring now to FIG. 3, a schematic top plan view of a cover 40 is shown. The cover 40 may be a cover as shown in FIG. 2. The cover 40 depicted in FIG. 3 includes a UV-transparent substrate 44 on which a UV-blocking coating 80 is disposed. The coating 80 is disposed on a region (e.g., region 40C depicted in FIG. 2) configured to be disposed over the channel (e.g., channel 50 depicted in FIG. 2). In the embodiments depicted in FIG. 3, the coating 80 is not disposed on the periphery of the substrate 44 so that the outer regions (e.g., regions 40A and 40B depicted in FIG. 2) configured to be disposed over the sidewalls (e.g., sidewalls 22, 24 depicted in FIG. 2) are transparent to UV radiation, so that UV radiation may be transmitted through the substrate 44 to adhesive (e.g., adhesive 30) disposed on top of the sidewalls.

Figure 4:
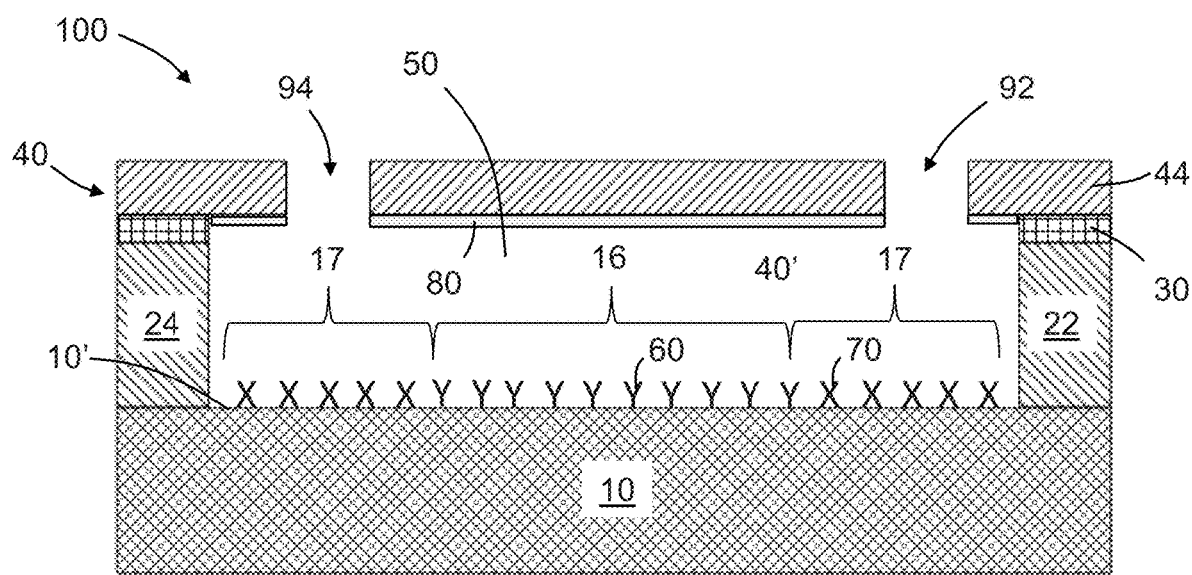
FIG. 4 is a schematic cross sectional view of an embodiment of a microfluidic sensor.

Referring now to FIG. 4, a schematic cross section of a microfluidic sensor device 100 is depicted. The device 100 contains components similar to the devices depicted in FIGS. 1 and 2. For numbered components depicted in FIG. 3 that are not explicitly discussed with regard to FIG. 3, reference is made to the description above regarding FIG. 1 and FIG. 2. The cover 40 depicted in FIG. 4 defines first 92 and second 94 ports, which may serve as an inlet and outlet for microfluidic channel 50. In the depicted embodiment, the ports 92, 94 are disposed over portions 17 of the resonator structure 10 to which blocking material 70, rather than biomolecule 60, is disposed. Accordingly, if UV radiation is employed to cure adhesive 30 to bond the cover 40 to the sidewalls 22, 24, UV radiation transmitted though the ports 92, 94 to the surface 10' of the resonator structure 10 would interact with blocking material 70 rather than biomolecule 60 and would less likely adversely affect the performance of the sensor device 100. The cover 40 includes a UV blocking coating 80 on a region disposed over the region 16 of the surface 10' of the resonator structure 10 to which the biomolecule 60 is bound to protect the biomolecule from UV radiation used to cure the adhesive 30.

Figure 5:
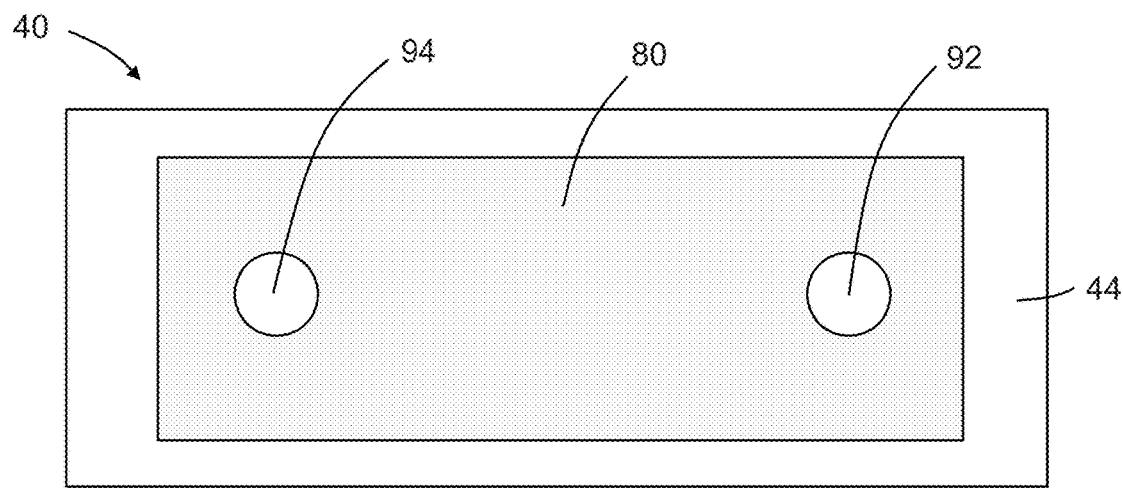
FIG. 5 is a schematic top plan view of an embodiment of an embodiment of a cover for a microfluidic sensor.

Referring now to FIG. 5, a schematic top plan view of a cover 40 is shown. The cover 40 may be a cover as shown in FIG. 4. The cover 40 depicted in FIG. 5 includes a UV-transparent substrate 44 on which a UV-blocking coating 80 is disposed. The coating 80 is disposed on a region configured to be disposed over the channel (e.g., channel 50 depicted in FIG. 4), particularly over a region (e.g., region 16 of FIG. 4) of the surface of the resonator structure to which biomolecule is attached. In the embodiments depicted in FIG. 5, the coating 80 is not disposed on the periphery of the substrate 44 so that the outer regions configured to be disposed over the sidewalls (e.g., sidewalls 22, 24 depicted in FIG. 4) are transparent to UV radiation, so that UV radiation may be transmitted through the substrate 44 to adhesive (e.g., adhesive 30) disposed on top of the sidewalls. The cover 40 defines ports 92, 94 through the substrate 44, which are preferably configured to be disposed over a less active region (e.g. region 17 depicted in FIG. 4) of the surface of the substrate or over a region of the substrate on which blocking material (e.g., blocking material 70 depicted in FIG. 4) is disposed.

Figure 6:
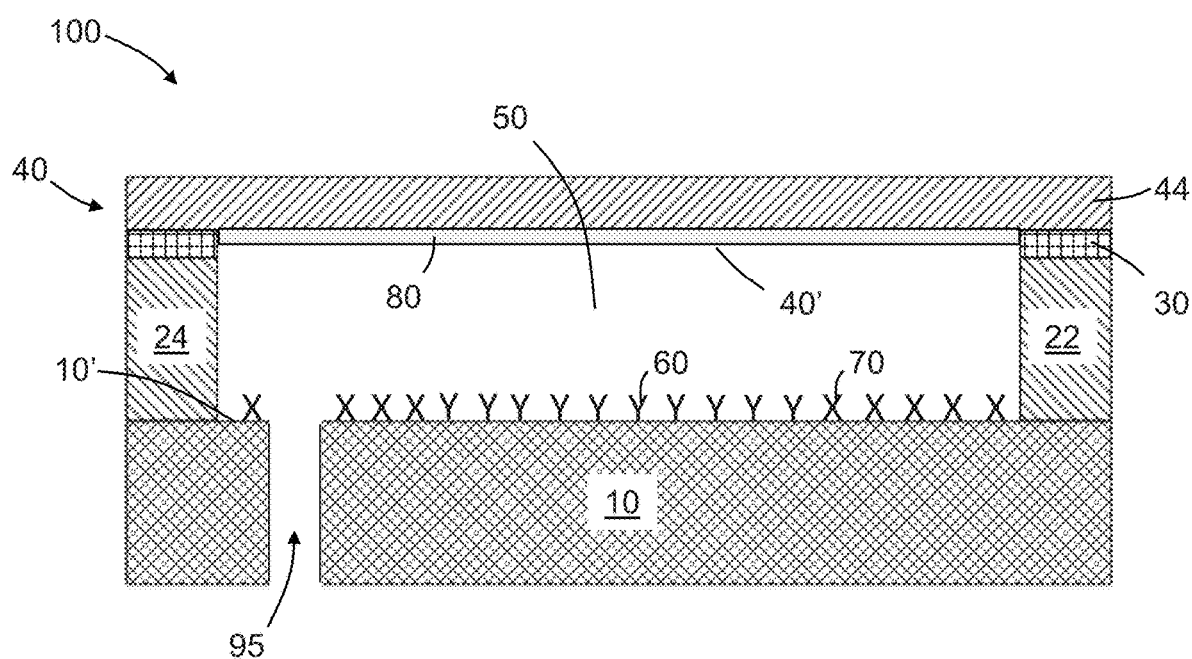
FIG. 6 is a schematic cross sectional view of an embodiment of a microfluidic sensor

Referring now to FIG. 6, a schematic cross section of a microfluidic sensor device 100 is depicted. The device 100 contains components similar to the devices depicted in FIGS. 1, 2, and 4. For numbered components depicted in FIG. 5 that are not explicitly discussed with regard to FIG. 5, reference is made to the description above regarding FIGS. 1, 2, and 4. The via 95 is defined through the resonator structure 10. The via 95 may serve as an inlet or an outlet to the microfluidic channel. More than one via may be formed through the resonator structure 95 to provide access to the channel 50.

While an inlet or outlet to the microfluidic channel is shown in cover in FIG. 2 and in the resonator structure in FIG. 4, it will be understood that an inlet or outlet into the microfluidic channel may be formed in any suitable manner or through any suitable structure, such as through a sidewall.

Figure 7A:
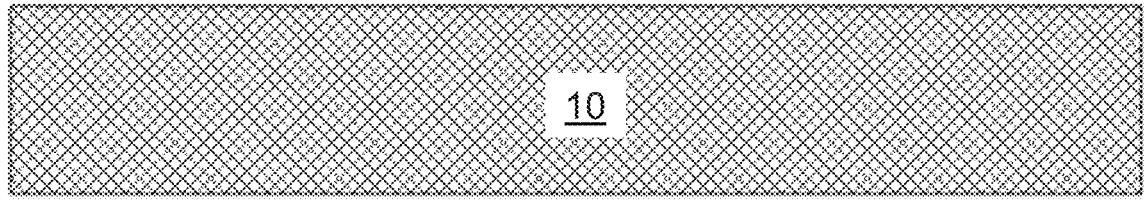
FIGS. 7A-F are schematic cross sectional views illustrating an embodiment of a process for manufacturing a microfluidic sensor.
Figure 7B:
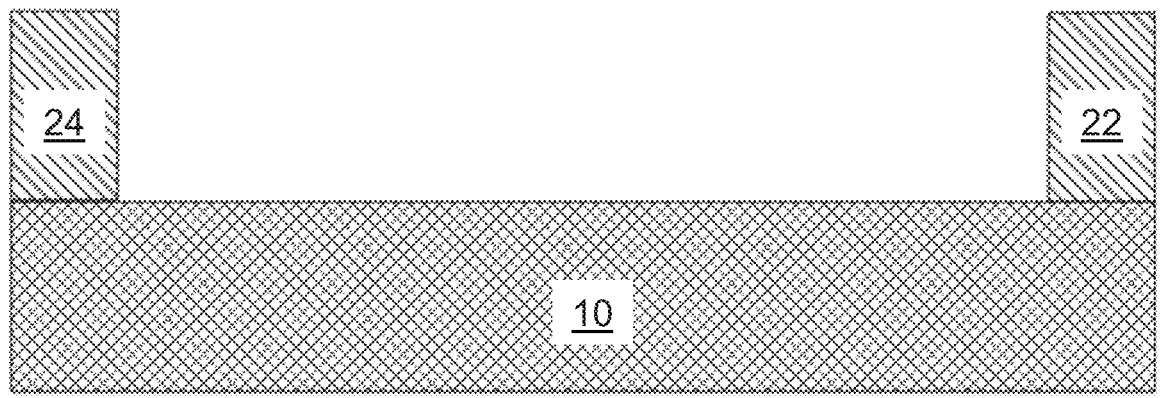
Figure 7C:
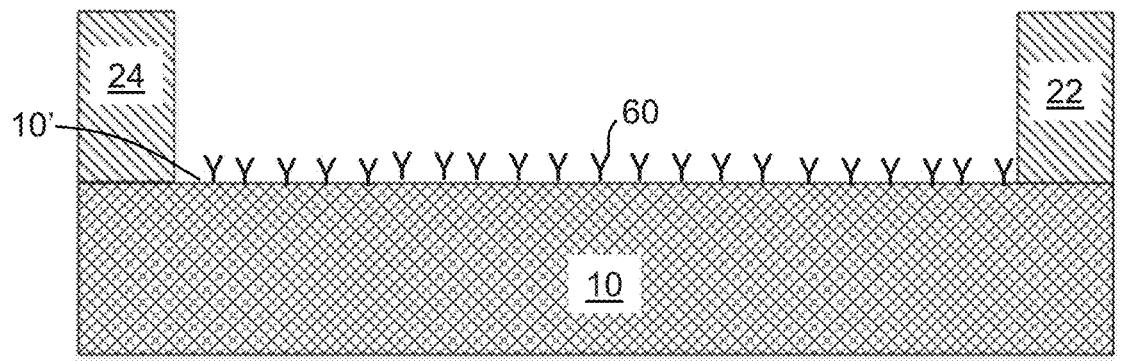

Referring now to FIGS. 7A-7F, a brief overview of an example of an embodiment of a process for fabricating a microfluidic sensing device is shown. In FIG. 7A, a resonator structure 10 is provided. Additional details regarding one way to fabricate an embodiment of such a resonator structure are described below with reference to FIGS. 8-9. As depicted in FIG. 7B, sidewalls 22, 24 are positioned on the resonator structure 10. A discussed above, the sidewalls 22, 24 may be formed from one continuous structure or from separate structures. Sidewalls 22, 24 may be formed of any suitable material, such as a laser-cut "stencil" layer of thin polymeric materials and/or laminate materials, optionally including one or more self-adhesive surfaces (e.g. adhesive tape), or using an SU-8 negative epoxy resist or other photoresist material. As shown in FIG. 7C, biomolecule 60 is applied to a surface 10' of the resonator structure 10.

The surface 10' of the resonator structure 10 or a portion thereof may be chemically functionalized or activated for binding to a deposited biomolecule 60. Alternatively, a layer (not shown) comprising a functional material for binding to the biomolecule 60 may be deposited on the surface 10', or a portion thereof, to activate the surface for binding the biomolecule 60. For example, the surface 10' may be functionalized to including a hydroxylated oxide surface suitable for attachment of an organosilane-based SAM, or comprises gold or another noble metal suitable for attachment of a thiol-based self-assembled monolayer (SAM). Following formation of the SAM, biomolecule 60 may be deposited on the SAM.

Figure 7D:
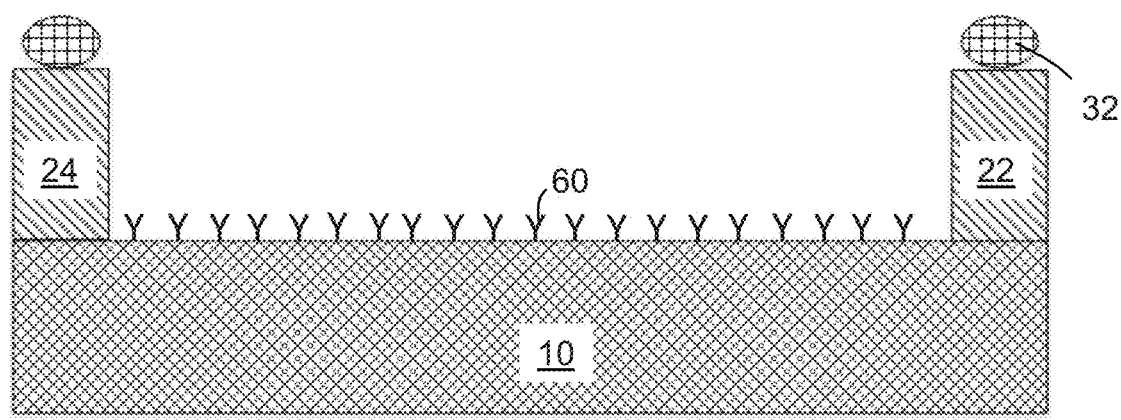

As shown in FIG. 7D, a UV-curable adhesive 32 may be applied to the top of the first 22 and second 24 sidewalls. Any suitable UV-curable adhesive 32 may be applied. For example, the UV-curable adhesive may include an adhesive resin and a UV photoactivator, such as a free-radical activator. In some embodiments, the UV-curable adhesive is a UV-curable epoxy. UV curable adhesives are commercially available from a number of manufacturers, such as Henkel, MasterBond, Parson Adhesives, Inc., and Epoxies Innovative Bonding Solutions, Etc.

Alternatively, a UV-curable adhesive 32 may be applied to regions 40A and 40B of the cover 40 on surface 40' (not shown) to avoid the possibility of stray droplets of adhesive from landing on the surface 10' of the resonator structure 10.

Figure 7E:
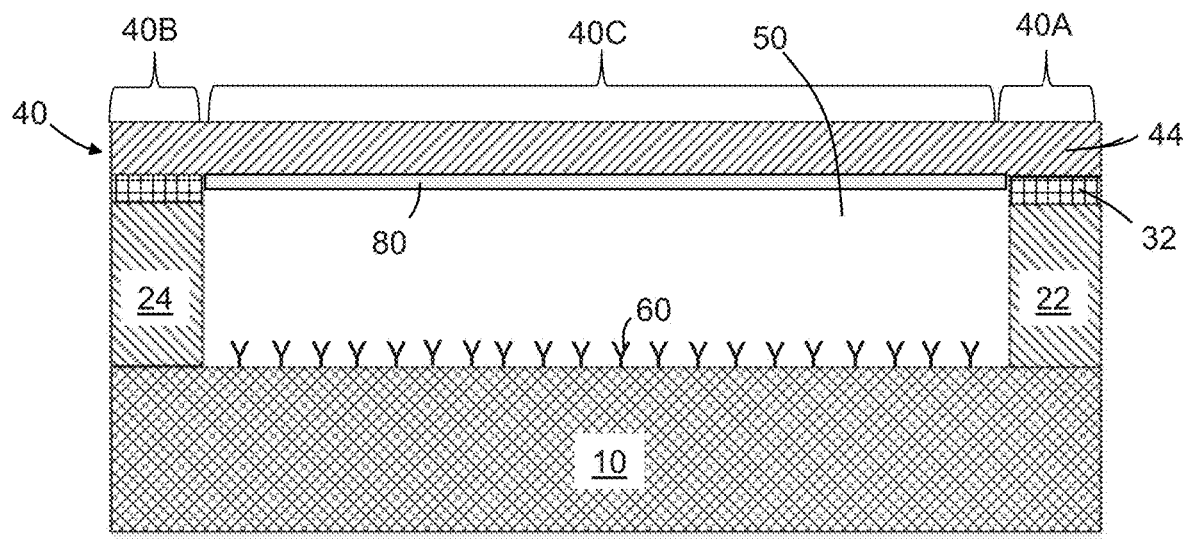
Figure 7F:
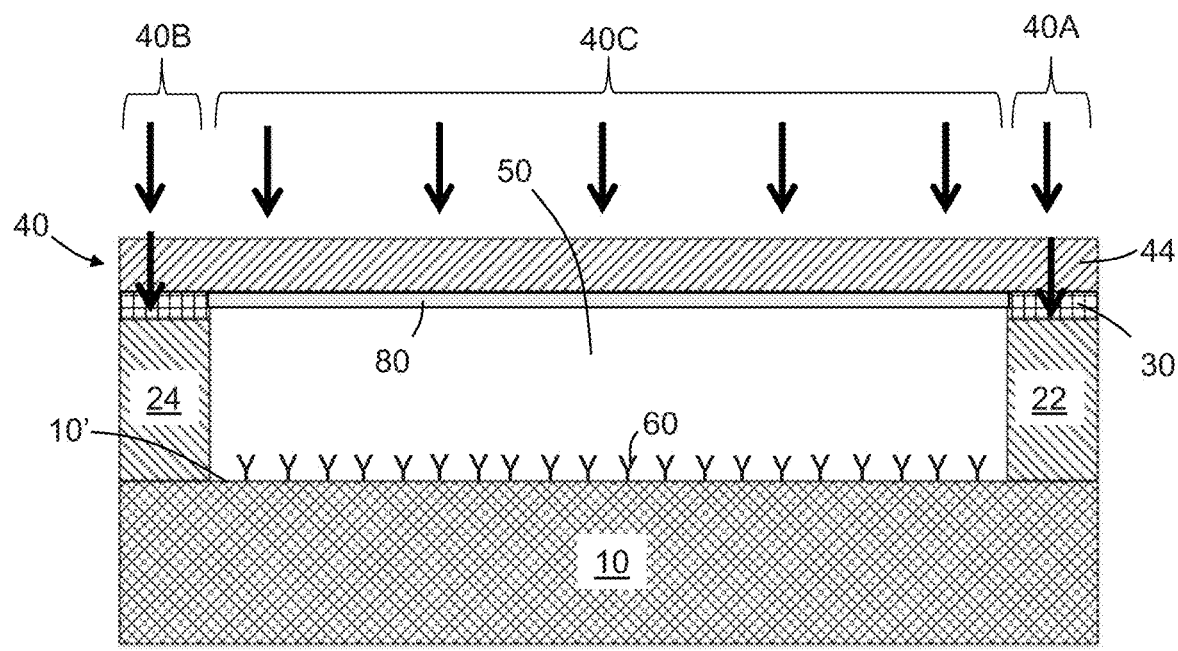

As illustrated in FIG. 7E a cover 40 having a UV-transparent substrate 44 and a UV blocking coating 80 may be disposed on the UV-curable adhesive 32 on top of the first 22 and second 24 sidewalls (alternatively, a cover 40 to which adhesive 32 is applied to regions 40A and 40B may be placed on the sidewalls 22, 24). First 40A and second 40B portions of the cover 40 are transparent (e.g., not coated) to UV-radiation and a coated portion 40C blocks transmission of UV coating through the cover 40. The first 40A and second 40B portions of the cover 40 are aligned with the first 22 and second 24 sidewalls and the blocked portion 40 is disposed over the channel 50. UV radiation (indicated by vertical arrows in FIG. 7F) may be applied external to the cover 40 and be transmitted through the first 40A and second 40B portions to allow the UV radiation to cure the UV-curable adhesive. The source of UV radiation may be a broadband source or a narrow band source. The cured adhesive 30 bonds the cover 40 to the sidewalls 22, 24. The UV-radiation is blocked from passing through cover 40 in region 40C due to the UV-blocking coating 80, which protects the biomolecule 80 attached to the surface 10' of the resonator structure 10.

UV-exposure and UV-curing may be performed at temperatures below, for example, 40° C. (or any other suitable temperature) so that the biomolecules 60 are not subjected to temperatures that may denature or otherwise adversely affect properties of the biomolecules 60.

The description provided above is fairly generic regarding a resonator structure. Some of the description provided below details embodiments of bulk acoustic resonators that may be employed as a resonator structure. Preferably, the resonator structure comprises a BAW resonator structure arranged over at least a portion of a substrate, and a biomolecule arranged over at least a portion of an active region of the BAW resonator structure. Various layers may be arranged between the biomolecule and a top side electrode (which is coincident with an active region of a BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material.

Figure 8:
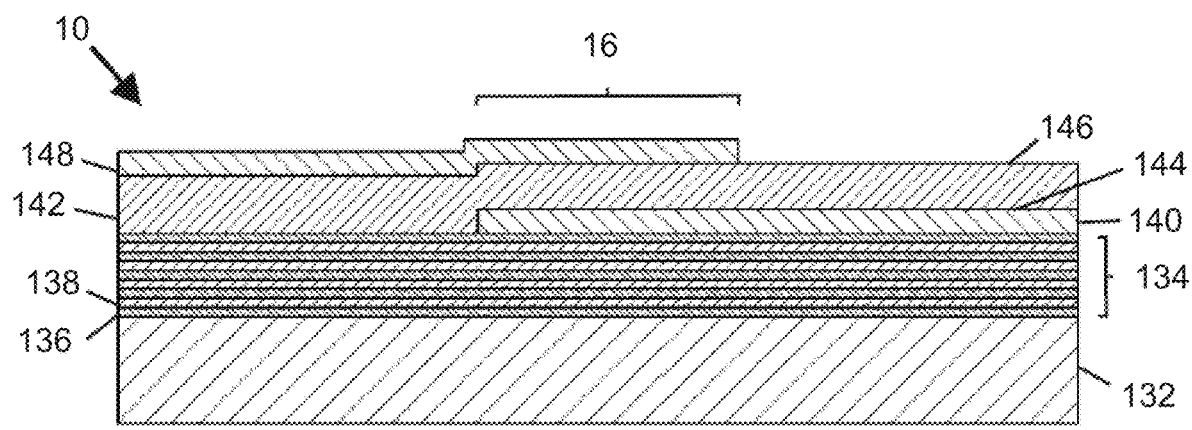
FIG. 8 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

FIG. 8 is a schematic cross-sectional view of a portion of a bulk acoustic wave MEMS resonator structure 10 useable with embodiments disclosed herein. The resonator structure 10 includes a substrate 132 (e.g., typically silicon or another semiconductor material), an acoustic reflector 134 arranged over the substrate 132, a piezoelectric material 142, and bottom and top side electrodes 140, 148. The bottom side electrode 140 is arranged along a portion of a lower surface 144 of the piezoelectric material 142 (between the acoustic reflector 134 and the piezoelectric material 142), and the top side electrode 148 is arranged along a portion of an upper surface 146 of the piezoelectric material 142. An area in which the piezoelectric material 142 is arranged between overlapping portions of the top side electrode 148 and the bottom side electrode 140 is considered an active region 16 of the resonator device 10 to which a biomolecule is preferably applied. The acoustic reflector 134 serves to reflect acoustic waves and therefore reduce or avoid their dissipation in the substrate 132. In certain embodiments, the acoustic reflector 134 includes alternating thin layers 136, 138 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 132. In certain embodiments, other types of acoustic reflectors may be used. Steps for forming the resonator device 30 may include depositing the acoustic reflector 134 over the substrate 132, followed by deposition of the bottom side electrode 140, followed by growth (e.g., via sputtering or other appropriate methods) of the piezoelectric material 142, followed by deposition of the top side electrode 148.

In certain embodiments, the piezoelectric material 142 comprises a hexagonal crystal structure piezoelectric material (e.g., aluminum nitride or zinc oxide) that includes a c-axis having an orientation distribution that is predominantly non-parallel (and may also be non-perpendicular to) to normal of a face of the substrate 132. Under appropriate conditions, presence of a c-axis having an orientation distribution that is predominantly non-parallel to normal of a face of a substrate enables a BAW resonator structure to be configured to exhibit a dominant shear response upon application of an alternating current signal across a distal electrode and a proximal electrode thereof (e.g., as may be desirable in the context of a BAW resonator structure providing sensing utility). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

The bulk acoustic wave MEMS resonator structure 10 shown in FIG. 8 lacks any layers (e.g., including functionalization material) overlying the active region 16 that would permit the resonator device 10 to be used as a biochemical sensor. If desired, at least portions of the resonator device 10 shown in FIG. 8 (e.g., including the active region 16) may be overlaid with various layers, such as one or more of: a hermeticity layer, an interface layer, a self-assembled monolayer (SAM), and/or a functionalization material layer (which may include specific binding material or non-specific binding material).

Figure 9:
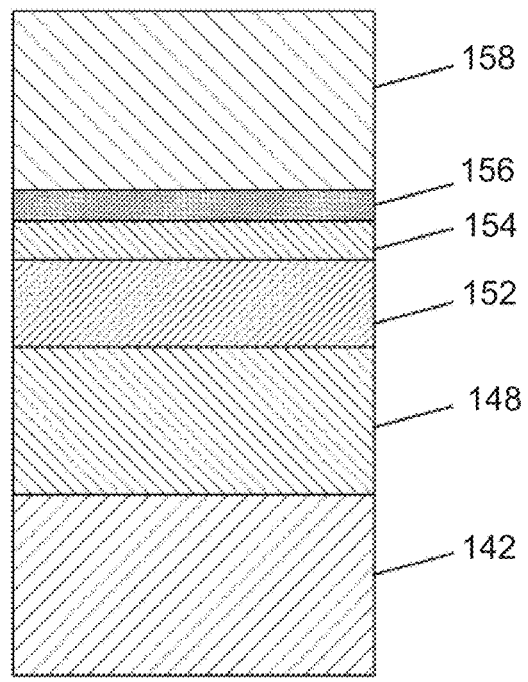
FIG. 9 is a schematic cross-sectional view of an upper portion of a BAW resonator device including a piezoelectric material and a top side electrode overlaid with a hermeticity layer, an interface layer, a self-assembled monolayer, and a layer including biomolecule.

FIG. 9 is a schematic cross-sectional view of an upper portion of a BAW resonator device including a piezoelectric material 142 and a top side electrode 148 overlaid with a hermeticity layer 152, an interface layer 154, a self-assembled monolayer (SAM) 156, and a layer 158 comprising a biomolecule. In certain embodiments, one or more blocking materials (not shown) may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide ($SiO_2$). Alternative materials incorporating hydroxylated oxide surfaces for forming interface layers include silicon dioxide [$SiO_2$], titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage may be important for a hermeticity layer (if present) to avoid corrosion of the underlying electrode. ALD, chemical vapor deposition, or any other suitable deposition process may be used to apply the hermeticity layer. In certain embodiments, an interface layer may be deposited. In certain embodiments, a hermeticity layer and an interface layer may be sequentially applied in a vacuum environment, thereby promoting a high-quality interface between the two layers. If multiple layers are deposited, they may be deposited sequentially without breaking vacuum, or may be applied separately with vacuum break.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one specific binding material. In certain embodiments, specific binding materials may be applied on or over a SAM using a microarray spotting needle or other suitable methods. In certain embodiments, an interface layer may be patterned (e.g., using photolithography for defining the interface layer) with a high dimensional tolerance over only a portion of a resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization material (e.g., chemical functionalization material) may provide non-specific binding utility.

Certain embodiments are directed to a fluidic device including multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the resonator structures. Such a device may be microfluidic in scale, and comprise at least one microfluidic passage (e.g., having at least one dimension, such as height and/or width, of no greater than about 1000 microns, no greater than about 500 microns, or no greater than about 250 microns, or no greater than about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic channel over a first bulk acoustic wave MEMS resonator structure with an active region thereof arranged along a bottom surface of a microfluidic passage, and then enclosing the microfluidic passage using a cap or cover layer that may define fluidic ports (e.g., openings) enabling fluid communication with the microfluidic passages. In certain embodiments, functionalization (e.g., specific binding) material may be pre-applied to the active region of a bulk acoustic wave MEMS resonator structure before formation of a microfluidic passage; in other embodiments, functionalization material may be applied over an active region of a bulk acoustic wave resonator structure following formation of the microfluidic passage.

Walls of a microfluidic channel may be formed of any suitable material, such as laser-cut "stencil" layers of thin polymeric materials and/or laminate materials, optionally including one or more self-adhesive surfaces (e.g., adhesive tape). Optionally such walls may be formed prior to deposition of a SAM layer, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic channel, and the integrally formed partial cover/wall structure may be applied (e.g., adhered or otherwise bonded) over at least a portion of a bulk acoustic wave resonator structure to enclose the at least one fluidic channel.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)—containing materials. An ideal blocking buffer would bind to all potential sites of non-specific interaction away from an active region. To optimize a blocking buffer for a particular analysis, empirical testing may be used to determine signal-to-noise ratio. No single chemical blocking material is ideal for every situation, since each antibody-antigen pair has unique characteristics.

Figure 10:
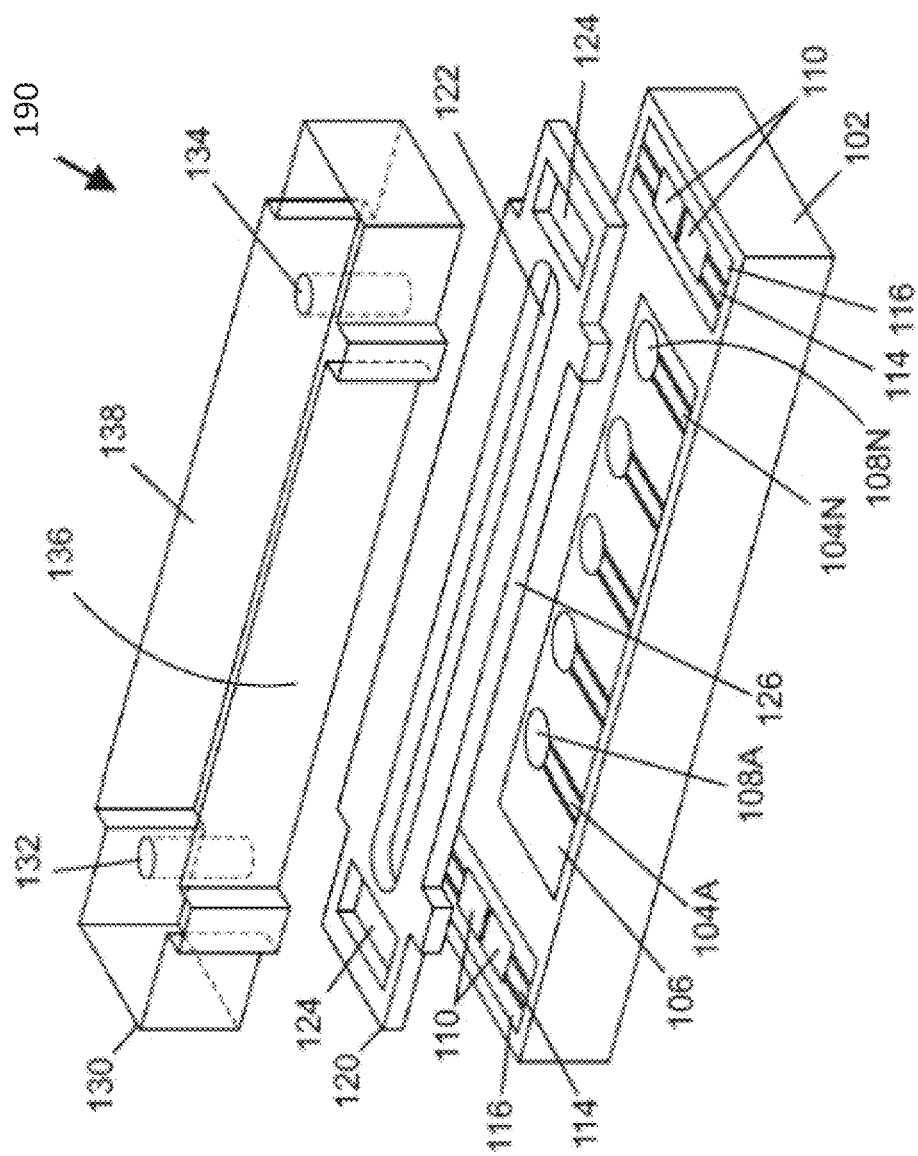
FIG. 10 is a schematic perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer.

FIG. 10 is a perspective assembly view of a microfluidic device 190 incorporating a substrate 102 with multiple bulk acoustic wave MEMS resonator devices, an intermediate layer 120 defining a central microfluidic channel 122 registered with active regions 108A-108N (to which biomolecule is attached) of the MEMS resonator devices, and a cap or cover layer 130 arranged to cover the intermediate layer 120. Top central portions of the substrate 102, which includes an acoustic reflector (not shown) and a piezoelectric material (not shown), include a top side electrode 106 and bottom side electrodes 104A-104N. Regions in which the foregoing electrodes overlap one another with the piezoelectric material arranged therebetween embody active regions 108A-108N. Any suitable number of active regions 108A-108N may be provided and fluidically arranged in series or parallel, although five active regions are illustrated in FIG. 10. Top peripheral (or top end) portions of the substrate 102 further include reference top side electrodes 116 and reference bottom side electrodes 114 in communication with reference overlap regions 110. Such reference overlap regions 110 are not exposed to fluid, and are present to provide a basis for comparing signals obtained from the active regions 108A-108N exposed to fluid within the central microfluidic channel 122. The substrate 102 is overlaid with the intermediate (e.g., wall-defining) layer 120, wherein the central microfluidic channel 122 is intended to receive fluid, and defines peripheral chambers 124 arranged to overlie the reference overlap regions 110 in a sealed fashion. The intermediate layer 120 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 120 further includes a lateral inset region 126 that enables lateral portions of the top side electrode 106 and bottom side electrodes 104A-104N to be accessed upon assembly of the microfluidic device 100. The cap or cover layer 130 includes a lateral inset region 136 registered with the lateral inset region 126 of the intermediate layer 120, and includes microfluidic ports 132, 134 accessible along a top surface 138 and registered with end portions of the central microfluidic channel 122 defined in the intermediate layer 120 to permit fluid (e.g., liquid) to be supplied to the central microfluidic channel 122 over the active regions 108A-108N. Preferably, at least the electrodes 104A-104N, 106 are overlaid with a hermeticity layer, an interface layer, a self-assembled monolayer, and biomolecule for binding analyte as disclosed herein. Microfluidic devices according to other configurations may be provided, as will be recognized by those skilled in the art upon review of the present disclosure.

Figure 11:
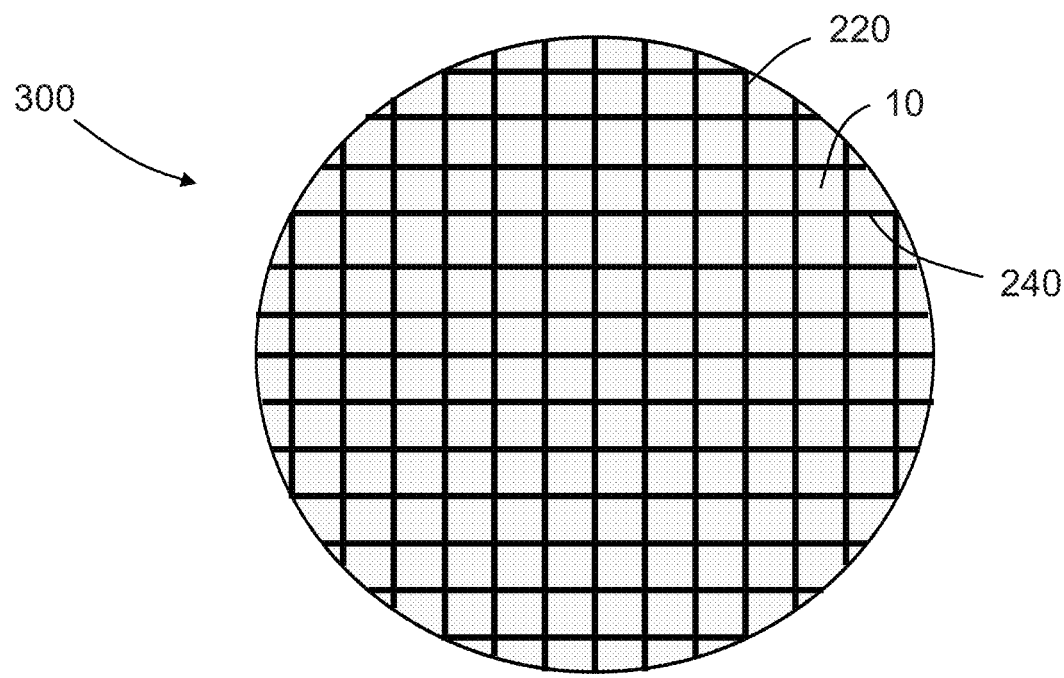
FIGS. 11-13 are schematic diagrams of a wafer (FIG. 11), a cover (FIG. 12) and a covered wafer (FIG. 13) showing that the methods described herein may be applied to wafer-level bonding for wafer-level packaging (WLP).
Figure 12:
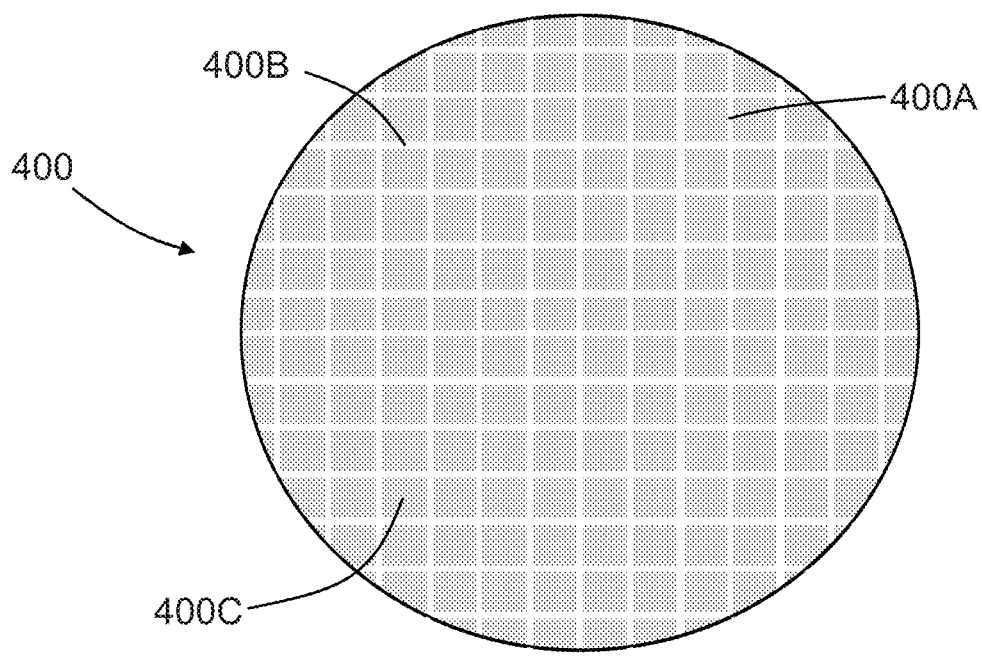
Figure 13:
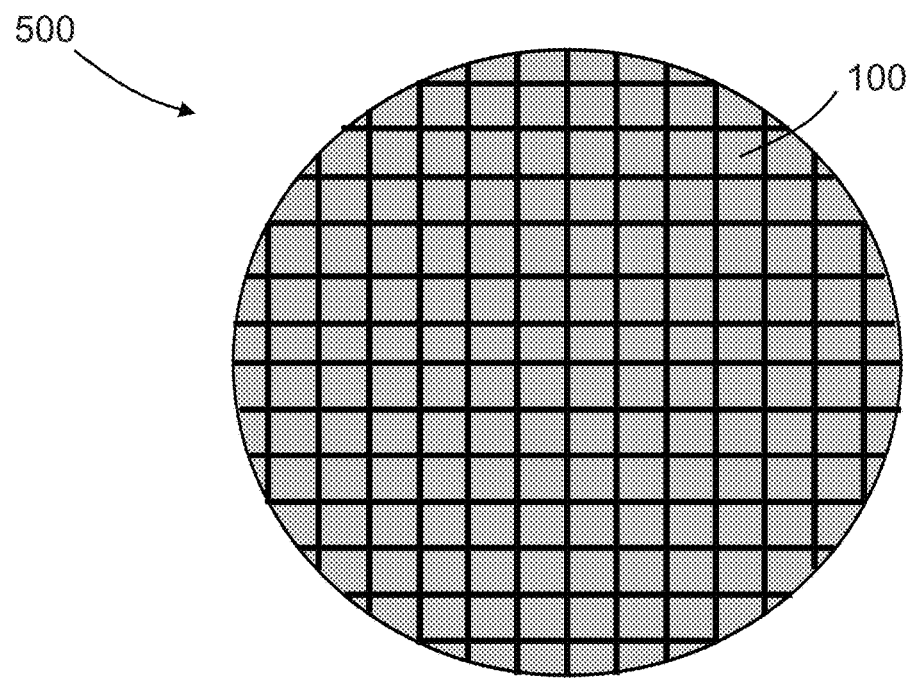

FIGS. 11-13 shows that the aforementioned methods can also be applied to wafer-level bonding for wafer-level packaging (WLP). An example of a wafer-level bonding is shown with a reversed-aperture lid wafer. FIG. 11 depicts a wafer 300 that may be cut into a number of dies, each containing a resonator structure 10 as described above. The wafer 300 includes a plurality of walls 220, 240 extending from the surface of the wafer. When the wafer 300 is cut into dies, walls 220, 240 may serve as sidewalls of the die (e.g., sidewalls 22, 24 described above). The biomolecule (e.g., biomolecule 60 described above) may be applied to the surface of each resulting resonator structure 10 on the wafer-scale level in a manner as described above.

Referring now to FIG. 12, a wafer-scale cover 400 is shown. The cover 400 includes a number of UV-blocked regions 400C and UV-transparent areas 400A, 400B (which correspond to depicted vertical and horizontal lines). The UV-transparent regions 400A, 400B may be aligned with walls 220, 240 of wafer 300, and UV-blocked regions 400C may be aligned with what will result in resonator structures 10 of wafer when the wafer is cut into dies.

FIG. 13 depicts a structure 500 that includes the cover 400 bonded to the wafer 300 in a manner such that the UV-transparent regions 400A, 400B of the cover 400 are aligned with walls 220, 240 of wafer 300. To bond the cover 400 to the wafer 300, UV-curable adhesive may be applied to the UV-transparent regions 400A, 400B of the cover 400, and the cover 400 may be placed on the wafer 300 such that the adhesive (not shown) is aligned with the tops of the walls 220, 240 of the wafer 300. The resulting structure 500 may be exposed to UV radiation to cure the adhesive and bond the cover 400 to the wafer 300. The resulting structure 500 may be cut along the shown lines (corresponding to walls 220,240 of wafer 300 and UV-transparent regions 400A, 400B of cover 400) to generate a number of fluid sensing devices 100 (e.g., devices 100 as depicted and described with regard to FIGS. 1, 2, 4, 6, and 7F above).

Figure 14A:
FIGS. 14A-J are schematic cross sectional diagrams of wafer level packing (FIGS. 14A-I) and a resulting resonator device (FIG. 14J).
Figure 14B:
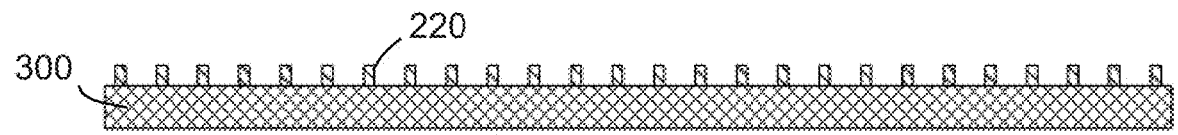
Figure 14C:
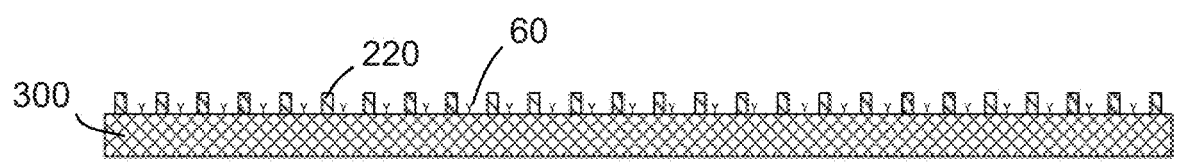

For purposes of illustration of wafer-level packing, reference is now made to FIGS. 14A-J. In FIG. 14A a cross sectional view of a wafer 300 is shown. In FIG. 14A walls 220 are deposited on a surface of the wafer 300. Biomolecule 60 is deposited on the surface of the wafer 300 between the walls 220 (FIG. 14C).

Figure 14D:
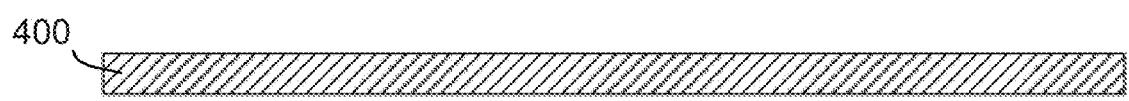
Figure 14E:
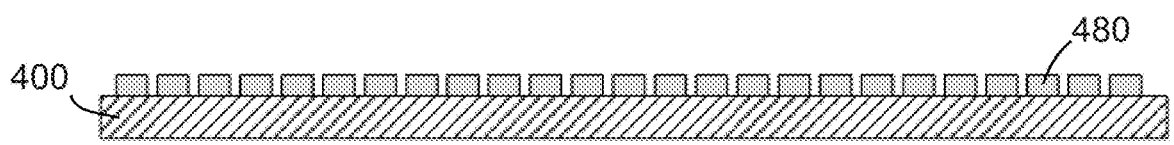
Figure 14F:
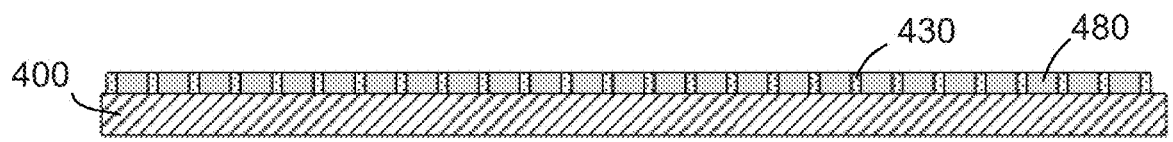

In FIG. 14D, a wafer-scale cover 400 is depicted. Preferably, the cover 400 is UV-transparent. As shown in FIG. 14E, a UV-blocking coating 480 is deposited on a surface of the cover 400 (e.g. in region 400C depicted in FIG. 12). As shown in FIG. 14F, UV-curable adhesive 430 is deposited on the surface of the cover 400 between the UV-blocking coating 480 (e.g., the adhesive 430 is deposited in regions 400A, 400B depicted in FIG. 12).

Figure 14G:
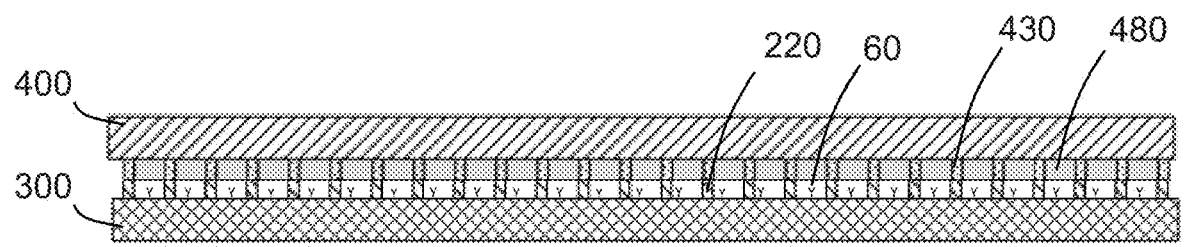
Figure 14H:
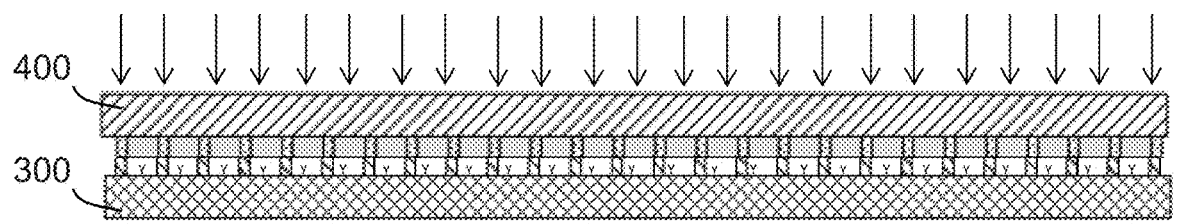
Figure 14I:
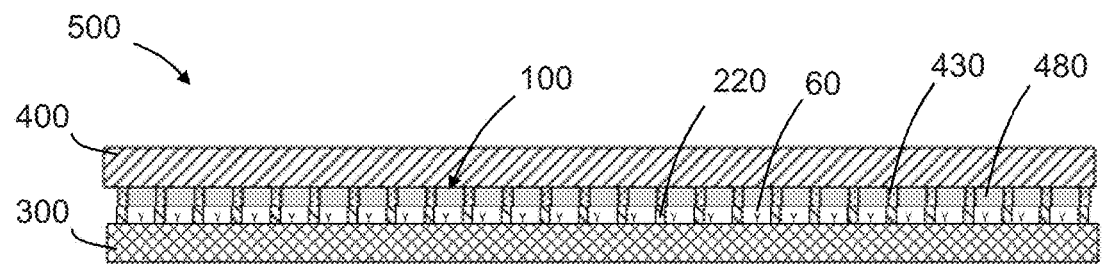
Figure 14J:
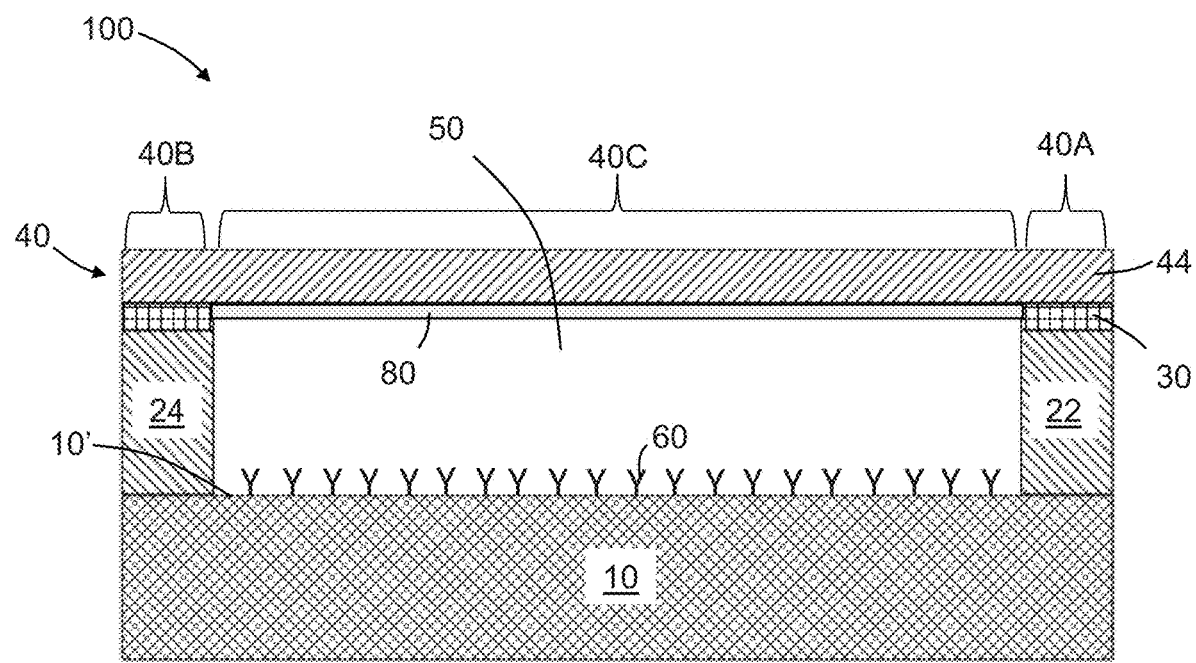

As shown in FIG. 14G, the cover 400 may be inverted and placed on the wafer 300 such that the adhesive 430 is disposed on top of the walls 220 and the coating 480 is disposed over the region of the wafer 300 on which the biomolecule 60 is deposited. As shown in FIG. 14H, UV radiation (indicated by vertical arrows) may be applied external to the cover 400. The UV radiation is transmitted through the UV transparent areas of the cover 400 on which the adhesive 430 is deposited (e.g., regions 400A, 400B depicted in FIG. 12). UV-radiation is blocked by coating 80 to protect the biomolecule 60. The resulting structure 500, which may be cut into individual fluid sensing devices 100 is shown in FIG. 14I. For example, the resulting structure 500 may be cut along lines corresponding to walls 220 of wafer 300 and UV-transparent regions of cover 400 (e.g., the resulting structure 500 may be cut along lines corresponding to walls 220, 240 shown in FIG. 11).

A fluid sensing device 100 resulting from cutting of a wafer-scale device 500 is depicted in FIG. 14I, which may correspond to devices 100 as depicted and described with regard to FIGS. 1, 2, 4, 6, and 7F above. For the numbered elements depicted in FIG. 14J, reference is made to the description above regarding FIGS. 1, 2, 4, 6, and 7F.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, the term "and/or" includes any and all combinations of one or more of the associated listed items.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, "providing" in the context of providing an article or a device means to make, purchase, or otherwise obtain the article or device.

Those skilled in the art will recognize improvements and modifications to the preferred embodiments of the present disclosure. All such improvements and modifications are considered within the scope of the concepts disclosed herein and the claims that follow.

What is claimed is:

1. A fluidic sensing device comprising:
   a fluidic channel having a first side, a second side, a top, and a bottom;
   a first sidewall defining the first side of the fluidic channel;
   a second sidewall spaced apart from the first sidewall and defining the second side of the fluidic channel;
   a bulk acoustic resonator structure having a surface defining at least a portion of the bottom of the channel, wherein the bulk acoustic resonator structure comprises piezoelectric material arranged between a first electrode and a second electrode;
   a biomolecule attached to the surface of the bulk acoustic resonator;
   a cover disposed over the first and second sidewalls and attached to the first and second sidewalls, wherein the cover defines at least a portion of the top of the fluidic channel and wherein a portion of the cover disposed over the channel blocks transmission of ultraviolet (UV) radiation configured, wherein a first portion of the cover disposed over the first sidewall is transparent to UV radiation, and wherein a second portion of the cover disposed over the second sidewall is transparent to UV radiation.

2. A fluidic sensing device according to claim 1, wherein the cover is attached to the first and second sidewalls via a cured UV-curable adhesive.

3. A fluidic sensing device according to claim 2, wherein the UV-curable adhesive comprises a UV-curable epoxy adhesive.

4. A fluidic sensing device according to claim 1, wherein cover comprises a UV blocking coating on the portion disposed over the fluidic channel.

5. A fluidic sensing device according to claim 4, wherein the UV blocking coating comprises a compound that absorbs UV radiation.

6. A fluidic sensing device according to claim 5, wherein the radiation blocking coating comprises a coating that is transparent to visible light.

7. A fluidic device according to claim 4, wherein the UV blocking coating reflects UV radiation.

8. A fluidic sensing device according to claim 4, wherein the coating is on a surface of the cover that faces the fluidic channel.

9. A fluidic sensing device according to claim 4, wherein the cover has an outer surface and an inner surface, wherein the inner surface faces the fluidic channel, and wherein the coating is on one or both of the inner surface and the outer surface.

10. A fluidic sensing device according to claim 1, wherein the cover has an outer surface and an inner surface, wherein the inner surface faces the fluidic channel, and wherein the cover defines an inlet extending from the outer surface to the inner surface, wherein the inlet is in communication with the fluidic channel.

11. A fluidic sensing device according to claim 1, wherein the resonator structure comprises a via extending through the resonator structure, wherein the via is in communication with the fluidic channel.

12. A fluidic sensing device according to claim 1, wherein the biomolecule comprises an antibody or an analyte-binding fragment thereof.

* * * * *